United States Patent [19]

Scepanski

[11] Patent Number: 5,977,183

[45] Date of Patent: Nov. 2, 1999

[54] SOLID ANTIMICROBIAL COMPOSITIONS

[75] Inventor: William H. Scepanski, Bloomington, Minn.

[73] Assignee: Sunburst Chemicals, Inc., Minneapolis, Minn.

[21] Appl. No.: 08/781,654

[22] Filed: Jan. 10, 1997

Related U.S. Application Data

[63] Continuation-in-part of application No. 08/534,664, Sep. 27, 1995.

[51] Int. Cl.$^6$ .......................... A01N 33/12; A01N 25/00; A01N 25/30; A01N 25/34; C11D 3/48; C11D 9/50; C11D 17/00

[52] U.S. Cl. ............................. 514/643; 422/28; 422/34; 422/37; 504/150; 504/158; 514/642; 514/772; 514/772.3; 514/964; 514/975; 424/78.08; 424/401; 424/405; 424/409; 424/486; 424/DIG. 5; 510/382; 510/391; 510/445; 510/447; 510/504

[58] Field of Search .................... 424/405, 78.08, 424/401, 409, 486, DIG. 5; 422/28, 34, 37; 504/150, 158; 514/642, 643, 772, 772.3, 964, 975; 510/382, 391, 445, 447, 504

[56] References Cited

U.S. PATENT DOCUMENTS

| | | | |
|---|---|---|---|
| 4,624,713 | 11/1986 | Morganson et al. | 134/25.2 |
| 4,769,159 | 9/1988 | Copeland | 8/137 |
| 5,312,624 | 5/1994 | Richter et al. | 424/405 |
| 5,358,653 | 10/1994 | Gladfelter et al. | 252/90 |
| 5,419,908 | 5/1995 | Richter et al. | 424/405 |
| 5,462,681 | 10/1995 | Gutzmann et al. | 252/11 |
| 5,474,698 | 12/1995 | Rolando et al. | 252/90 |
| 5,622,708 | 4/1997 | Richter et al. | 424/405 |
| 5,674,831 | 10/1997 | Schulz et al. | 510/501 |
| 5,698,513 | 12/1997 | Schultz et al. | 510/501 |
| 5,709,871 | 1/1998 | Hill | 424/409 |
| 5,837,651 | 11/1998 | Hill | 504/116 |

OTHER PUBLICATIONS

Armak Technical Datasheet–Duomeen, 1981, Armak Co., Bulletin 81–19.

*Primary Examiner*—John Pak
*Attorney, Agent, or Firm*—Patterson & Keough, P.A.

[57] ABSTRACT

Substantially solid (or nonflowable) antimicrobial compositions have advantages over corresponding liquids and powders. Such a composition may be contained within a plastic bottle with a label indicating that the contents have antimicrobial or deodorizing properties containing a substantially solid, non-flowable composition having greater than about 0.02 percent by weight antimicrobial compounds. The preferred compositions consist essentially of an antimicrobial compound selected from the group consisting of quaternary ammonium salts, fatty amines and diamines, chlorhexidine gluconate, phenol, derivatives of phenol, parachloro metaxylenol and mixtures thereof, and between 0 and 99.98 percent by weight of a cleaning composition. The compositions can be effectively used with solid dispensers. The solid dispensers have a bowl with a drain at the bottom and an upward pointing spray nozzle. The spray nozzle directs water into an inverted bottle of the composition to produce an aqueous solution of antimicrobial compounds which drains from the bottom of the bowl. A second source of aqueous solution or fresh water can combine with the solution draining from the bowl to product a more dilute solution of antimicrobial compounds. The relative flow into the spray nozzle and the secondary source can be adjusted to produce a final diluted solution with a desired dilution. Antimicrobial solutions can be used in a variety of industrial and institutional applications including laundry and hard surface cleaning. Four methods of producing these substantially solid, antimicrobial compositions are described.

3 Claims, 1 Drawing Sheet

SOLID ANTIMICROBIAL COMPOSITIONS

CROSS-REFERENCES TO RELATED APPLICATIONS

This appn. is a continuation-in-part of 08/534,664 as originally filed on Sep. 27, 1995 is incorporated herein by reference.

FIELD OF THE INVENTION

The invention relates generally to compositions containing antimicrobial agents. The invention more specifically relates to substantially solid, non-flowing and homogeneous compositions containing particular antimicrobial agents where the compositions can be used in dispensers which direct water at a surface of the composition to dissolve a selected amount of the composition to produce an antimicrobial solution.

BACKGROUND OF THE INVENTION

An extensive number of antimicrobial compositions are commercially available in liquid or powder form. The liquid compositions typically have active ingredients in the range of 5 percent to 15 percent by weight of the product, but highly concentrated liquid products can contain up to 80% active ingredients. Concentrated liquid products must be diluted before use. Ready to use liquid products can have concentrations of active ingredients at least as low as 0.02 percent by weight of the product. All of these liquid products contain significant amounts of water, alcohols and/or other materials as diluents. Because these products are diluted, they utilize more packaging materials and result in higher shipping weights to transport a given amount of active material than is required for a highly concentrated solid.

A significant disadvantage of powder or granular products for commercial applications is that they are not as accurately controllable in dispensing equipment as liquids. Powder systems can require manually scooping a quantity of powder for each use, thus not taking advantage of the ease, accuracy and hands-off labor savings of liquid dispensers. Also, powders can cake if exposed to high humidity or temperatures. Once they become caked, they cannot be easily removed from their shipping container. Non-homogeneous powders can segregate in their shipping containers, in other words, separate or stratify by particle size or density, resulting in a non-uniform mixture that may not be appropriate for ultimate use applications.

Some disinfectants and sanitizers are considered corrosive which creates hazards in shipping and handling. Spilled liquid material from leaking containers or mishandling the product can come into contact with skin or eyes causing tissue damage, pain and discomfort. Powders can create a safety hazard because particles of irritating or corrosive materials can exit their container or become airborne allowing the particles to come into direct contact with tissue, such as skin or lungs, causing burns or discomfort. A solid antimicrobial product would not be easily capable of creating this hazard since it cannot leak out of its container nor can it be spilled in handling.

Because of stringent regulatory controls over disinfectants and sanitizers, especially for institutional uses, solutions for application typically must be prepared with specific and exacting dilution ratios. Typical sanitizer and disinfectant concentrates are mixed with water to obtain a solution with a specific concentration for applications. These solutions are used to sanitize or disinfect objects and surfaces such as counter tops, tables, floors, walls, dishes, utensils and fabrics. Many institutions requiring these products include food processors, nursing homes, health care facilities, kitchens, and laundries. Hence, a composition containing an antimicrobial agent may be used to produce a disinfectant or sanitizing solution. These products are also effective at deodorizing because they can destroy odor causing bacteria and other microbes.

While liquid and powder products can be measured by hand and accurately diluted, this process is slow and potentially hazardous if the materials are corrosive. Liquid products can be properly diluted using dispensing apparatuses to produce solutions for application, but this does not eliminate all of the inconveniences and hazards of handling a liquid. Recently, dispensers have been developed for accurate and convenient dispensing of solids. For example, U.S. Pat. No. 5,342,587 to Laughlin et al. describes a solid dispensing device where the solid is provided in a plastic bottle that is inverted over a bowl. Water is sprayed on the solid to produce a solution that is drained from the bowl.

Some sanitizer or disinfectant concentrates have cleaning agents added to the antimicrobial compounds to create cleaner-disinfectants. Commercially available liquid and powder cleaner-disinfectants clean soils from surfaces as well as kill microorganisms. The cleaning agents in these products can be alkaline, neutral or acidic, and include anionic or nonionic surfactants along with other optional additives such as alkaline builders and metal ion sequestering agents. Liquid and powder cleaner-disinfectants have the same disadvantages as liquid and powder forms of other sanitizing products.

SUMMARY OF THE INVENTION

Substantially solid or nonflowing and homogeneous antimicrobial compositions avoid the deficiencies of either liquids or powders. These compositions provide for convenient and safe handling and can be dispensed accurately and conveniently by using dispensers described herein. The preferred antimicrobial products are in a plastic container, such as a bottle or jar. The container will contain a substantially solid or non-flowable composition, the composition including greater than about 0.02 percent by weight antimicrobial compounds. The composition will preferably contain greater than about 0.5 percent by weight antimicrobial compounds, more preferably greater than about 2 percent by weight antimicrobial compounds and even more preferably greater than about 5 percent by weight antimicrobial compounds.

The antimicrobial compounds are preferably selected from the group consisting of quaternary ammonium salts, fatty amines, fatty diamines, chlorhexidine gluconate, phenol, derivatives of phenol, parachloro metaxylenol and/or mixtures thereof. The quaternary ammonium salts will preferably have at least one alkyl substituent on the quaternary nitrogen with $C_6$ to $C_{18}$ hydrocarbon units. The preferred amines and diamines have at least one alkyl substituent with carbon chain lengths in the range of $C_{10}$–$C_{18}$.

The preferred substantially solid (or nonflowable) and homogeneous antimicrobial compositions consist essentially of greater than about 0.02 percent by weight of an antimicrobial compound and about 99.98 percent or less, of a cleaning composition or diluent. The cleaning compositions may have a pH that is acid, alkaline, or neutral and may also include one or more compounds selected from the group consisting of surfactants, water soluble builders, inert ingredients and polyvalent metal sequestering agents.

The invention also includes methods of using and methods of making solid sanitizing compositions. One preferred method of using a substantially solid (or nonflowable) and homogeneous antimicrobial composition of this invention involves producing an antimicrobial use solution using a dispenser, the dispenser including a bowl with a drain, a tube connected to the drain and a spray nozzle for directing water upwardly from the bowl. An open bottle containing the substantially solid (or nonflowable) antimicrobial composition is inverted into the bowl such that water from the spray nozzle is directed into the open bottle and onto at least one surface of the antimicrobial composition. The spray of water dissolves a portion of the composition to form an aqueous solution of between about 150 and 30,000 parts per million antimicrobial compounds. The resulting antimicrobial solutions can be used advantageously in a variety of industrial and institutional applications including laundry and hard surface cleaning. The substantially solid (or nonflowable) and homogeneous antimicrobial composition preferably includes greater than about 0.02 percent by weight of antimicrobial compound selected from the group consisting of quaternary ammonium salts, fatty amines and diamines, chlorhexidine gluconate, phenol, derivatives of phenol, parachloro metaxylenol and mixtures thereof.

Another preferred method of using a substantially solid or nonflowable antimicrobial composition of the invention involves producing an antimicrobial use solution using a dispenser having a bowl with a drain at the bottom of the bowl, a spray nozzle for directing water upward from the bowl, a tube connected to the opening of the drain and an aqueous solution supply connecting with the tube from the drain to form a combined flow. A bottle containing a substantially solid (or nonflowable) antimicrobial composition is inverted into the bowl of the dispenser. The spray nozzle is directed upward into the open bottle and toward the antimicrobial composition. The relative flow volumes from the spray nozzle and the aqueous solution supply are adjusted to produce a desired concentration of antimicrobial solution in the combined flow.

There are several methods of producing the substantially solid (or nonflowable) and homogeneous antimicrobial composition of this invention. The first method involves forming a melted composition consisting of antimicrobial compounds and about 99.98 percent or less by weight of a cleaning composition or diluent. The antimicrobial composition preferably includes greater than about 0.02 percent by weight antimicrobial compounds and more preferably includes greater than about 1 percent by weight antimicrobial compounds. The melted composition is poured into a container where it solidifies upon cooling.

A second method of producing substantially solid (or nonflowable) and homogeneous antimicrobial compositions involves heating a solution of antimicrobial compounds to remove sufficient solvent to form a solvent-depleted composition. The solvent-depleted composition is poured into a container. The solvent-depleted composition subsequently cools to form a non-flowable composition.

A third method of producing substantially solid (or nonflowable) and homogeneous antimicrobial compositions begins by melting a solid carrier. A powder antimicrobial composition is mixed into the melted carrier to form a melted, antimicrobial composition. The melted antimicrobial composition is poured into a container. Upon cooling to room temperature, the composition forms a substantially solid (or nonflowable) and homogeneous antimicrobial composition.

The fourth method of producing a substantially solid (or nonflowable) and homogeneous antimicrobial composition involves mixing an aqueous solution of an antimicrobial compound with an anhydrous hydratable salt to form a homogeneous dispersion. The aqueous solution of the antimicrobial compound can be preformed or it can be formed in situ by adding a powder antimicrobial compound and water or another aqueous solution. The compounds in the substantially homogeneous solution or dispersion may or may not be dissolved. The homogeneous dispersion is then poured into a container. The container is subsequently stored until a substantially solid (or nonflowable) and homogeneous antimicrobial composition is formed in the container.

DEFINITIONS

Antimicrobial

The property of a substance, whereby the substance is capable of killing at least either 99.999% or 100% of a quantity of a test culture of bacteria or fungi at concentrations between about 150 and 800 ppm and under conditions specified by reference methods contained within Section 4 of Official Methods of Analysis of the Association of Official Analytical Chemists, Ed. Sidney Williams, 14th and 15th Eds., the entire disclosure of which is hereby incorporated by reference; or in the case of viruses, is capable of achieving greater than a 3 $\log_{10}$ difference in viral infectivity as measured between observed host cell cytopathic and cytotoxic effects in test protocols adhering to Environmental Protection Agency (EPA) guidelines as described by Formulations DC-108N/DC-109N/DC-110N in Lonza Biocides Marketing Manual (1996), the entire disclosure of which is hereby incorporated by reference.

Nonantimicrobial.

Describing a substance which is not capable of killing microorganisms at the specific concentrations and conditions defined with respect to antimicrobial above.

Inert.

Pertaining to substances present in a formulation which lack antimicrobial efficacy when used in an aqueous solution containing no other ingredients.

Use Solution.

A final, diluted aqueous solution containing a sufficient amount of at least one antimicrobial compound or substance required to effectively kill the required percent of existing organisms as described above with respect to antimicrobial.

Microbe or Microorganism.

An organism including, but not limited to, bacteria, viruses, fungi, and reproductive structures thereof.

Microbial.

Relating to microbes as defined above.

Sanitize.

To kill 99.999% of the microbes or achieve a 3 $\log_{10}$ reduction in infective viral titer on a surface as described with respect to antimicrobial.

Disinfect.

To kill 100% of the microbes or achieve a 3 $\log_{10}$ reduction in infective viral titer on a surface as described with respect to antimicrobial.

Substantially Solid.

Describing a nonliquid composition or substance in which the composition or substance is a relatively hard single mass and which is neither granular nor powder.

Water Soluble Builder.

An alkaline, neutral, or acidic substance enhancing the cleaning abilities of use solutions derived from the compositions of the present invention.

Substantially Nonflowable.

Describing a nonliquid composition or substance, the composition or substance immobile to the extent that the composition or substance will not flow or pour when a container containing the substantially nonflowable composition or substance is rotated or inverted.

Substantially Homogeneous.

Describing a composition or substance in which all ingredients therein are melted, dissolved or otherwise evenly and uniformly dispersed or distributed therewithin.

DETAILED DESCRIPTION OF THE INVENTION

Figure 1:
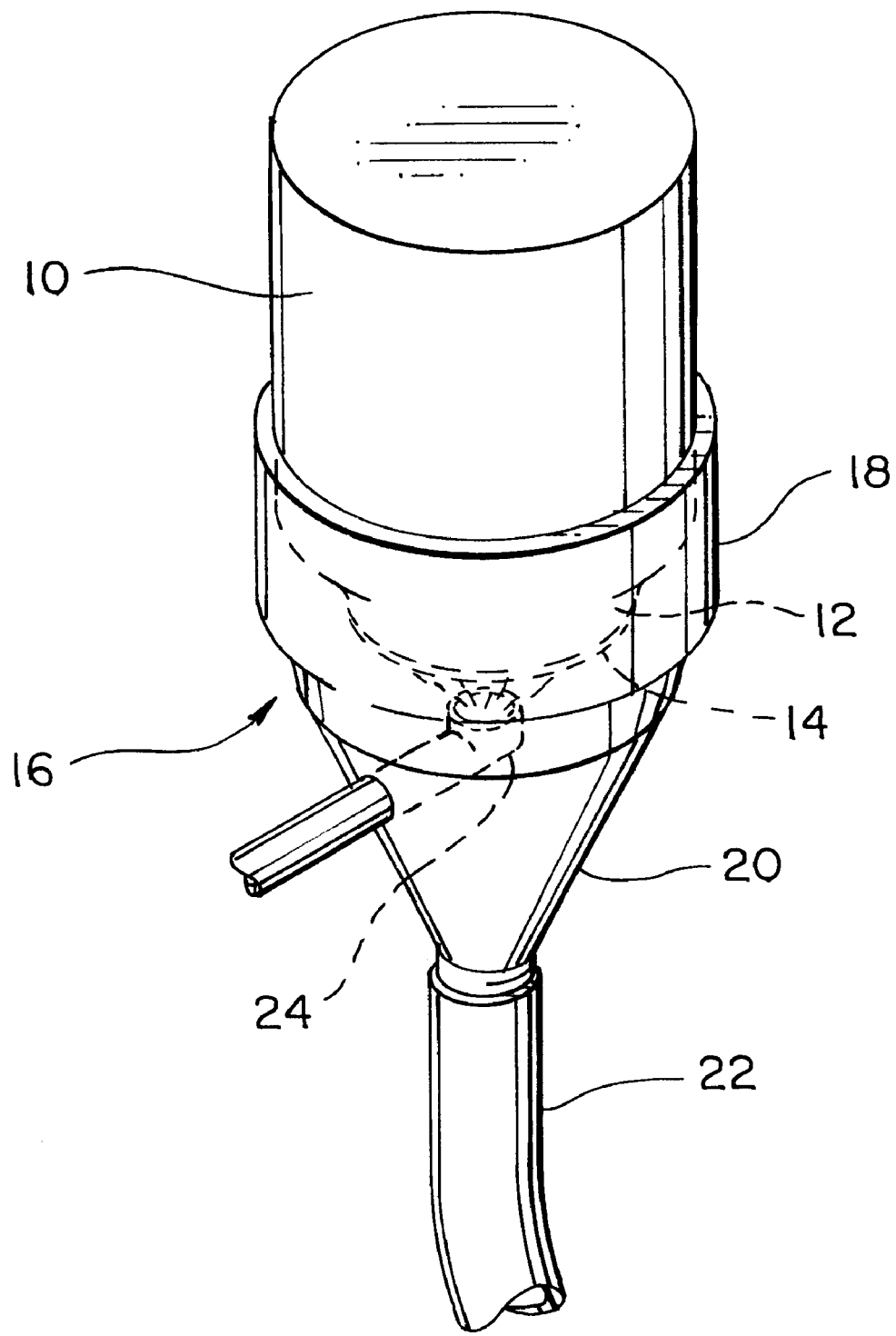
FIG. 1 is a schematic representation of a dispenser with a container filled with a composition within the invention, where a nozzle for directing water into the open end of the container within the dispenser is shown in broken lines.

The invention consists of antimicrobial compositions manufactured into a substantially solid and nonflowable form. It is preferred that the solid be produced in a container, e.g., a bottle or jar, such that the container can be used with a solid dispenser. In a typical solid dispenser, the container containing the substantially solid, nonflowable composition is inverted in the dispenser. The dispenser directs water at a surface of the composition to produce a solution having the desired concentration of the antimicrobial compounds. Alternatively, the solution can be further diluted if necessary. The invention is founded on the surprising simplicity of producing and using these solid products in a practical manner using particular types of antimicrobials. The solid antimicrobial sanitizers, deodorizers and disinfectant/cleaners of the invention are particularly suitable for use in recently developed dispensers.

The antimicrobial compounds are preferably approved by the U.S. Environmental Protection Agency for use as sanitizers or disinfectants. Appropriate antimicrobial agents or compounds include quaternary ammonium compounds, fatty amines, fatty diamines, chlorhexidine gluconate, phenol and halogen or methyl substituted phenols, and parachlorometa xylenol, although this list is not inclusive. The substantially solid antimicrobial composition will include at least about 0.02 percent to 100 percent of the above antimicrobial compounds by weight. More preferably, the substantially solid product will contain at least about 0.5 percent to 100 percent of the antimicrobial compounds. Even more preferably, the substantially solid product will contain between about 2 percent and 100 percent of the antimicrobial compounds. Generally, the appropriate antimicrobial agents or compounds are selected from the group consisting of quaternary ammonium salts, fatty amines, fatty diamines, chlorhexidine gluconate, phenol, derivatives of phenol, parachloro metaxylenol and mixtures thereof.

Appropriate commercially available quaternary ammonium compounds with antimicrobial properties include n-alkyl dimethyl benzyl ammonium chloride, n-alkyl dimethyl ethyl benzyl ammonium chloride, dialkyl dimethyl ammonium chloride, alkyl oxypropyl dihydroxyethyl methyl ammonium chloride and alkyl benzyl imidazolinium chloride. The alkyl groups include substituent hydrocarbon chains from $C_6$ to $C_{20}$, more preferably $C_8$–$C_{18}$, and even more preferably $C_{10}$–$C_{16}$. Substituent hydrocarbon chains with one or more $C18$–$C_{20}$ groups result in quaternary ammonium salts with less antimicrobial activity. However, quaternary ammonium salts with one or more $C_{18}$–$C_{20}$ are known to have good fabric softening characteristics and hence may be desirable as additives when fabric softening is a desired characteristic.

Specific sources of quaternary ammonium chloride include Bardac 205M™, BTC2125MP40™, JAQ Powdered Quat™, FMB451-8 Quat™, and FMB1210-50™. Bardac 205M™, manufactured by Lonza, Inc., is a mixture of alkyl ($C_{14}$, 50%; $C_{12}$, 40%; $C_{16}$, 10%) dimethyl benzyl ammonium chloride (20.0%); octyl decyl dimethyl ammonium chloride (15.0%); dioctyl dimethyl ammonium chloride (7.5%); didecyl dimethyl ammonium chloride (7.5%); and inert ingredients (50.0%). BTC2125MP40™ is marketed by the Stepan Company and includes 20 percent n-alkyl dimethyl benzyl ammonium chloride ($C_{12}$, 5%; $C_{14}$, 60%; $C_{16}$, 30%; $C_{18}$, 5%), 20 percent n-alkyl dimethyl ethyl benzyl ammonium chloride ($C_{12}$, 68%; $C_{14}$, 32%), and 60 percent inert ingredients. JAQ brand Powdered Quat contains n-alkyl dimethyl benzyl ammonium chloride dihydrate ($C_{16}$, 2%, $C_{14}$, 95% and $C_{12}$, 3%) and is made by Crystal Performance Chemicals. FMB 451-8 Quat™ is made by Crystal Performance Chemicals and contains 80 percent by weight benzyl ammonium chloride ($C_{12}$, 40%; $C_{14}$, 50%; $C_{16}$, 10%). FMB1210-50™ contains about 50 percent by weight water and 30 percent didecyl dimethyl ammonium chloride and 20 percent n-alkyl dimethyl benzyl ammonium chloride ($C_{12}$, 40%; $C_{14}$, 50%; $C_{16}$, 10%).

The anion in the quaternary ammonium compounds is of less importance than other substituent groups and can be selected from chlorides, sulfates, methosulfates, acetates and bromides or others. However, chloride is the most commercially available anion. Antimicrobial quaternary ammonium compounds are commercially available generally as liquid solutions and powders. The liquid solutions contain about 50 percent to 80 percent active ingredients, by weight, with the remaining portion of the solution including solvents such as water, ethanol and isopropanol. The powders typically contain between 40 percent and 100 percent by weight quaternary ammonium compounds.

Quaternary ammonium compounds in liquid solution or powder form are widely accepted for use as sanitizers and disinfectants. Their use solutions typically have low odors and are not hazardous to the user when used as directed. Because of their safety, these quaternary ammonium compounds need not be rinsed from surfaces prior to food contact. Moreover, the quaternary ammonium compounds are relatively inexpensive.

Useful phenolic compounds with antimicrobial activity include phenol, p-chlorophenol, dichlorophenol, o-phenylphenol, 2,4,6 trichlorophenol, 2,4,5 trichlorophenol, pentachlorophenol, o-benzyl-p-chlorophenol and para-chloro-meta xylenol. Other substituted phenols may also be appropriate for use in the substantially solid, nonflowable antimicrobial compositions of this invention. The substituted phenols preferably have melting points between 100° F. and 180° F. The alcohol hydrogen in phenol and in phenol derivatives is preferably sufficiently acidic to react with certain aqueous bases to form neutralized salts containing the phenoxide anion $C_6H_5O^-$. These neutralized, or partially neutralized, salts may often be substituted for the phenolic compounds. The cations in the salt forms may include sodium, potassium or ammonium.

Another class of appropriate antimicrobial agents includes alkyl amines and alkyl diamines, for example isodecyl oxypropyl amine acetate, isodecyl oxypropyl diamine, 1-(alkyl-amino)-3-amino propane, sold by AKZO Chemicals under the trade name Duomeen C™. Duomeen C™ is made from coconut oil. Hence, Duomeen C™ has an alkyl chain distribution representative of coconut oil fatty acids. Duomeen C™ is effective against bacteria, fungi and algae. One alkyl group of the appropriate amines and diamines is typically in the range of $C_8$–$C_{18}$.

The particular preferred antimicrobial agent will depend on the method of production and the composition of the final solid product. The composition of the final product will be selected to produce an end use solution with a desired concentration of the antimicrobial compound. If other materials are added to dilute the concentrations of antimicrobial compounds, these additives can be selected to provide desired properties to the final composition. For example, additional cleaning agents may be added to the composition to yield an antimicrobial product which cleans as well as disinfects (or sanitizes).

In the production of antimicrobial compositions, chelating agents (or polyvalent metal sequestering agents) and water soluble builders may be added to impart cleansing properties and to enhance the antimicrobial activity of the use solution. The cleaning compositions within the cleaner-disinfectants may be acidic, alkaline, or neutral in pH. A neutral pH cleaning composition would not significantly change the pH of the water used to dilute the product into a final use solution. These compositions are particularly useful for a wide variety of applications, including hard surface cleaning.

Preferred surfactants would be nonionic, although conventional anionic surfactants and cationic surfactants may be suitable with certain antimicrobial compounds. Conventional anionic surfactants may be compatible with phenolic antimicrobial agents. Concentrations of surfactants in the antimicrobial compositions will generally be between about 10 and 70 percent by weight. Additionally, the antimicrobial compositions may include other additives such as dyes and fragrances.

A variety of nonionic surfactants are known to be useful in cleaners. Nonionic surfactants which can be used within this invention include, but are not limited to, the following:

Nonylphenol ethoxylates with about 4–100 ethylene oxide groups per nonylphenol molecule, i.e., nonylphenol (ethoxylate)$_n$, n=4–100

Dinonylphenol ethoxylates with about 4–150 ethylene oxide groups per dinonylphenol molecule Linear alcohol ethoxylates with the alcohol chain consisting of 6–24 carbon atoms and with about 2.5 to 150 ethylene oxide groups per alcohol molecule Dodecylphenol ethoxylates with about 4–100 ethylene oxide groups per dodecylphenol molecule Octylphenol ethoxylates with about 4–100 ethylene oxide groups per octylphenol molecule Alkanolamides in which the carbon chain consists of a $C_{12}$–$C_{18}$ fatty acid reacted with mono or diethanolamine or isopropanolamine to yield a product having a melting point above about 100° F.

Ethoxylated alkanolamides in which the carbon chain consists of a $C_{12}$–$C_{18}$ fatty acid reacted with ethylene oxide and mono or diethanolamine or isopropanolamine Amine oxides having a carbon chain from $C_8$ to $C_{18}$ Fatty acid ethoxylates with about 2–40 ethylene oxide groups per fatty acid where the fatty acid has a carbon chain from $C_8$ to $C_{18}$ Ethylene oxide/propylene oxide (eo/po) block copolymers with average molecular weights between about 1,000 and 15,000

Nonylphenol ethoxylate propoxylates with average molecular weights between about 400–8000

Linear alcohol ethoxylate propoxylates with average molecular weights between about 400–8000 and carbon chain lengths from $C_8$ to $C_{18}$.

The specific nonionic surfactant will be selected to have the best cleaning properties, melting point and dissolving rate for an appropriate cost, given the intended use for the cleaning composition. Preferred nonionic surfactants include lower molecular weight nonylphenol ethoxylates and linear alcohol ethoxylates.

Anionic surfactants which could be included in this product include, but are not limited to, the following:

1. Alkyl sulfonate salts and alkylaryl sulfonate salts, with sodium, potassium, ammonium, protonated mono, di or triethanolamine or protonated isopropanolamine cations, such as the following salts:
   Linear primary $C_6$–$C_{18}$ sulfonate salts
   Secondary $C_6$–$C_{18}$ sulfonate salts
   Alpha olefin sulfonate salts
   Dodecylbenzene sulfonate salts
   Tridecylbenzene sulfonate salts
   Xylene sulfonate salts
   Cumene sulfonate salts
   Toluene sulfonate salts 2. Alkyl sulfate and alkylaryl sulfate salts supplied with either sodium, potassium, ammonium, protonated mono, di or triethanolamine or protonated isopropanolamine cations, such as the following salts:
   Linear primary $C_6$–$C_{18}$ sulfate salts 3. Alkyl $C_6$–$C_{18}$ naphthalene sulfonate sodium, potassium, or ammonium salts.

4. Alkyl $C_6$–$C_{18}$ diphenyl sulfonate sodium, potassium or ammonium salts.

5. Alkyl ether sulfate salts or alkylaryl ether sulfate sodium, potassium, ammonium, protonated mono, di or triethanolamine, or protonated isopropanolamine salts, such as the following:
   Alkyl $C_8$–$C_{18}$ alcohol (ethoxylate)$_{ca.1-6}$ sulfate salts.
   Alkyl $C_8$–$C_{12}$, phenoxy (ethoxylate)$_{ca.1-12}$ sulfate salts.

6. Alkyl ether sulfonate salts or alkylaryl ether sulfonate salts with Na, K, NH4, protonated mono, di or triethanolamine or protonated isopropanolamine cations, such as:
   Alkyl $C_8$–$C_{18}$ alcohol (ethoxylate)$_{ca.1-6}$ sulfonate salts.
   Alkyl $C_8$–$C_{12}$ phenoxy (ethoxylate)$_{ca.1-12}$ sulfonate salts.

7. $C_4$–$C_{18}$ dialkyl sulfosuccinate salts with Na, K, $NH_4$, protonated mono, di or triethanolamine or protonated isopropanolamine cations, such as disodium dioctyl sulfosuccinate.

8. Other anionic surfactants such as mono or dialkyl phosphate ester salts or isothionate or taurate salts.

The choice of anionic surfactant will usually involve the same factors as the choice of nonionic surfactant.

Cationic surfactants are known in the art. Appropriate cationic surfactants include isodecyloxypropyl dihydroxyethyl methyl ammonium chloride and isotridecyloxypropyl dihydroxyethyl methyl ammonium chloride, both of which also exhibit antimicrobial properties.

Alkaline builders are water soluble bases added to cleaning compositions to raise the pH of cleaning solutions which include them. While alkaline builders may have inherent cleaning abilities, their primary purpose is to improve the cleaning functions of the surfactants in a use solution. The antimicrobial compositions of this invention may include about 60 percent or less, by weight, alkaline builder. The amount of alkaline builder in the composition will depend on the relative amounts of cleaning agents desired to achieve the proper cleaning effect. Moreover, the particular method of production may determine the amount of alkaline builder which will be incorporated into the product.

Powdered, bead, liquid or granular alkaline builders may be used in the formulation of antimicrobial compositions of this invention. Generally, any water soluble base is appropriate, although certain bases are commonly used as alkaline builders in cleaning compositions. Some alkaline builders which may be included are: sodium or potassium silicate, sodium or potassium carbonate, trisodium or tripotassium phosphate, $Na_2HPO_4$, $K_2HPO_4$, sodium hydroxide, potassium hydroxide, monoethanolamines, diethanolamines, and triethanolamines.

Chelating, sequestering or scale inhibiting ingredients are added to the cleaner to neutralize the adverse consequences of having divalent and trivalent ions of calcium, magnesium, iron and other less significant polyvalent metal cations in a cleaning solution made from the composition of the present invention. These divalent and trivalent cations enter the cleaning system with the water used as the main solvent and with the soils present in the system that are to be removed and reduce the effectiveness of cleaning compositions. Subsequent reference to "hardness ions" primarily refers to calcium, magnesium and, to a lesser degree, iron and other cations which are found in "hard water".

Hardness ions may also precipitate fatty acids present in soils to prevent their removal by surfactants. Inorganic anions such as carbonates, phosphates, silicates, sulfates, hydroxides and others may also precipitate with hardness ions to form inorganic films, spots or deposits on hard surfaces and on cleaning machines. These hardness ions may also promote graying and discoloration of fabrics by deposition of inorganic particles. The term sequestering is used to generally define and describe the chelating and sequestering of polyvalent metal cations, cations which would otherwise interfere with the cleaning process if free in solution.

Sequestering agents prevent these adverse effects by binding the hardness ions, thus keeping them in solution and thereby preventing them from precipitating with the above-mentioned organic and inorganic anions. Hence, addition of sequestering agents to cleaning solutions prevents scale from building up on cleaning equipment, on hard surfaces or on fabrics. Addition of sequestering agents further promotes the rinsing of any residual hardness ion-sequestering agent complexes which may have dried onto a substrate during the cleaning process.

Sequestering agents may be present in the antimicrobial compositions of this invention at concentrations of 60 percent or less, by weight, of cleaning composition. Sequestering agents which can be used in this invention, include, but are not limited to, the following:

1. Sodium, potassium, and ammonium salts of orthophosphate or of polyphosphates such as pyrophosphate, tripolyphosphate, trimetaphosphate, hexameta phosphate, or other higher complex phosphates having up to about 22 phosphorus atoms in the anion.
2. Ethylenediamine-tetraacetic (EDTA) acid or its fully or partially neutralized salts, e.g., sodium, potassium, ammonium or mono-, di- or triethanolamine salts.
3. Nitrilotriacetic (NTA) acid $N(CH_2CO_2H)_3$ or its full or partially neutralized salts, e.g., sodium, potassium, ammonium or mono-, di- or triethanolamine salts.
4. Other aminocarboxylic acids and their salts, for example: pentasodium diethylenetriamine pentaacetate, trisodium hydroxyethyl ethylenediamine triacetate, disodium ethanoldiglycine, sodium diethanolglycine.
5. Organic polycarboxylic acids and their salts, such as, oxalic acid, citric acid and gluconic acid.
6. Polyacrylic acid polymers with molecular weights between about 800 and 50,000, and their sodium, potassium, ammonium or mono-, di- or triethanolamine salts.
7. Copolymers of acrylic and maleic acid with molecular weights greater than about 800 and their sodium, potassium, ammonium or mono-, di- or triethanolamine salts.
8. Copolymers of acrylic acid and itaconic acid with molecular weights between about 800 and 50,000 and their sodium, potassium, ammonium or mono-, di- or triethanolamine salts.
9. Copolymers of maleic acid and itaconic acid with molecular weights between about 800 and 50,000 and their sodium, potassium, ammonium or mono-, di- or triethanolamine salts.
10. Amino trimethylene phosphoric acid and its sodium, potassium, ammonium or mono-, di- or triethanolamine salts.
11. 1-Hydroxyethylidine-1,1-diphosphonic acid and its sodium, potassium, ammonium or mono-, di- or triethanolamine salts.
12. Hexamethylenediamine tetra(methylenephosphonic acid) and its sodium, potassium, ammonium or mono-, di- or triethanolamine salts.
13. Diethylene triamine penta(methylene phosphoric acid) and its sodium, potassium, ammonium or mono-, di- or triethanolamine salts.
14. Dequest 2041™, made by Monsanto, which is a substituted phosphoric acid or salt.

Inert compounds may also be added to dilute the concentration of the antimicrobial compounds in the final solid composition. These inert compounds may be present with the antimicrobial compounds in either liquid or powder forms. Commercial suppliers may or may not indicate the chemical composition of inert compounds present. Suitable inert compounds to be added include sodium sulfate, urea, polyethylene glycol (preferably with a molecular weight greater than about 2000), and sodium chloride. The inert compounds may or may not affect the pH of the final use solution being produced.

This invention will include a substantially solid and homogeneous, nonflowable composition. The composition will impart antimicrobial properties to a use solution formed by dissolving all or a portion of the composition in water. The antimicrobial composition invention may further be a cleaner-disinfectant or cleaner-sanitizing composition, which imparts both antimicrobial and cleaning properties to use solutions made therefrom.

In use, all or a part of the substantially solid antimicrobial composition may be dissolved by a quantity of water to achieve a predetermined concentration of antimicrobial and other compounds in the use solution. Alternatively, the solution resulting from dissolving the substantially solid, nonflowable and homogeneous composition of the present composition may be further diluted to achieve a use solution.

The utility of the use solution of the present invention may further enable both a sanitizing and disinfectant solution to be made. Dissolving a predetermined amount of the substantially solid, nonflowable and homogeneous composition of the present invention may produce a use solution which is either a sanitizing solution or a disinfectant solution. A sanitizing use solution includes concentrations of antimicrobial compounds, preferably quaternary ammonium compounds, between about 150 parts per million (ppm) and 200 ppm by weight. A disinfectant use solution contains concentrations of antimicrobial compounds, preferably quaternary ammonium compounds between about 450 ppm and 800 ppm by weight.

Methods for the production of composition of this invention are described below. The first two methods are particularly suitable for the production of disinfectants and sanitizers, while the second two are more appropriate for the production of cleaner-disinfectants. Generally any of the methods could be used to produce sanitizers and cleaner-disinfectants. The choice of antimicrobial agent may also determine the method selected to produce the substantially solid, nonflowable composition.

The first method involves melting powdered antimicrobial compounds or compositions to form a liquid which is poured into an appropriate container or mold where it solidifies upon cooling. Preferred antimicrobial powders will have melting points between about 100° F. and 300° F. and more preferably between about 140° F. and 250° F.

It is surprising that powders including quaternary ammonium compounds melt into clear liquids. These clear liquids have properties allowing them to be poured easily and to form substantially hard waxy, nonflowing solids upon cooling. Pure powders of antimicrobial compounds or powders containing other ingredients may be used within this method. Additional ingredients may be added in powdered form before heating, or in powder or liquid form after the antimicrobial powder is melted.

After the melt is formed, the fluid may be mildly agitated to assure uniform consistency of the liquid. Agitation may be continued while any additives are mixed into the melt. The composition may then be cooled slightly before pouring to increase its viscosity so that undissolved ingredients will not separate during the packaging, cooling and solidification process. The melt is then poured into a container or a mold where it solidifies upon cooling, typically into a substantially solid waxy, nonflowing, and homogeneous composition. Preferably, the melt is poured into a plastic container with a capacity of about four fluid ounces to five gallons, the container ideally having a top opening of between 25 mm and 350 mm in diameter. More preferably, the container would have a capacity of 32 fluid ounces to 192 fluid ounces. More preferably yet, these containers are suitable for use in the dispensers described below.

The second method of production uses liquid solutions of antimicrobial compounds. These liquid solutions are heated until the solvents therewithin are evaporated, typically to between about 120° F. and 300° F. In a vessel under vacuum, a lower temperature is sufficient. Under atmospheric pressure, a preferred temperature range includes between about 210° F. and 300° F. Mixing during this evaporation process is desirable, especially during the early part thereof.

After the solvent has been mostly evaporated, a liquid remains. The remaining liquid may be poured into a container or mold similar to the procedure described above. Upon cooling, the liquid forms a stiff paste-like composition which does not flow from an inverted open bottle. Additives, especially cleaning compounds, may be added to the liquid antimicrobial solution, either before or after eating is commenced.

The third method of production uses a meltable solid carrier. The carrier is typically heated to a temperature significantly above its melting point, preferably about 20° F. or more above its melting point. An antimicrobial powder, liquid or liquid solution is added. The antimicrobial powder may be 100 percent antimicrobial compound, or it may contain other additives. If a liquid solution containing an antimicrobial is used, it should not be added in too large a quantity such that the solvent interferes with hardening of the final, poured composition. The mixture is agitated to form a homogeneous liquid and the temperature is kept sufficiently high to maintain the mixture in a liquid state. The liquid is then poured into a container or mold as previously described where it hardens into a substantially solid, nonflowable antimicrobial composition upon cooling.

Many substances will function as carriers. Preferred materials are water soluble with melting points between about 140° F. to 250° F. These carriers may be inert, they may be cleaning agents, or they may be other antimicrobial compositions. Effective carriers, selected to have appropriate melting points, include, but are not limited to, surfactants, fatty amines or fatty amine salts, such as hexadecylamine and cocoamine acetate, polyethylene glycol (molecular weight greater than about 2000), urea, and powdered antimicrobial compounds as described above. Additional ingredients, such as cleaning compounds, may be added, either before or after the melt is formed.

A fourth method for producing a solid antimicrobial composition involves a mixture of an aqueous, liquid antimicrobial solution using an anhydrous, or partially hydrated (but further hydratable), acid, neutral, or alkaline salt. Appropriate salts include, but are not limited to, sodium tripolyphosphate, sodium trimetaphosphate, sodium sulfate, sodium carbonate, sodium bicarbonate, sodium tetraborate and trisodium phosphate. Other cations may be substituted for sodium cations without affecting the results. The hydratable salt is added to a powder mixer, such as a ribbon or paddle mixer. The liquid antimicrobial solution is then added to the powdered salt and mixed until a flowable, semi-liquid (thin paste) consistency develops.

The above-described methods of making the composition of this invention include adding ingredients which may or may not be totally dissolved or melted. Often mixing or stirring, then cooling for increased viscosity, is necessary to ensure that added ingredients are not dissolved or melted, are dispersed evenly and do not settle out or separate into phases before the composition of the present invention solidifies. When all ingredients are melted, dissolved or are substantially evenly and uniformly distributed within the composition of the present invention, the composition is thereby appropriately termed substantially homogeneous.

The resulting semi-liquid (thin paste-like) mixture or dispersion is poured into a container or a mold and stored. During storage, the water supplied with the aqueous, antimicrobial solution hydrates the hydratable salt to form a substantially solid and homogeneous cake. The hydration process which forms the substantially solid composition typically requires one to three days. A variation of this process involves the substitution of an antimicrobial powder and water for the aqueous antimicrobial solution. The antimicrobial powder, powder salt and water are mixed to form the semi-liquid mixture. Other additives may be added to the semi-liquid mixture if desired.

Alternatively, the solid compositions of this invention may be molded into tablets. For example, these tablets may be formed in premeasured quantities and dissolved in water to form a sanitizing or disinfecting solution. However, tablets are less preferred than the other embodiments described herein because they generally dissolve slowly. It is thus more preferable to form the solid in a container which may be used in an appropriate dispenser to produce a sanitizing or disinfecting use solution more quickly.

BRIEF DESCRIPTION OF THE FIGURE

Referring to FIG. 1, container 10 will be generally cylindrical with tapered portion 12 ending at opening 14. Dispenser 16 includes bowl 18 into which container 10 is inverted. Bottom 20 of bowl 18 has a funnel shape to direct solutions into tubing 22 attached at the end of funnel-shaped bottom 20 of bowl 18. Spray tip 24 projects into funnel portion 20 of bowl 18. Spray tip 24 is placed such that it will spray water into container 10 to dissolve a portion of the product within container 10. Funnel 20 may direct the solution into tubing 22.

A specific example of a particularly suitable dispenser is described in U.S. Pat. No. 5,342,587 issued to Laughlin et al., the entire disclosure of which is hereby incorporated by reference. In this dispenser, a water inlet is attached to a fitting with a secondary outlet which directs water to a spray tip within the dispenser bowl. In one embodiment, the primary outlet of the fitting goes to an inlet to a Y-fitting that has a second inlet connected to the funnel at the end of the bowl. The outlet to the Y-fitting can be connected to the end of a hose. Using this dispenser, an antimicrobial agent stored as a solid in the container may be selectively dissolved in a stream of water yielding solution concentrations between 150–30,000 ppm antimicrobial compounds, which may be directed out the end of a hose. This is particularly convenient for sanitizing a large area which can be hosed down with a sanitizer dispensed from the end of the hose. For smaller applications, the hose can be directed into a bucket or similar container. The resulting antimicrobial solution may be further diluted to achieve a use solution with a desired antimicrobial compound concentration.

EXAMPLE 1

A 200 g sample of powdered n-alkyl dimethyl benzyl ammonium chloride dihydrate, sold by Crystal Performance Chemicals under the trademark JAQ Powdered Quat™, was placed in a 600 ml beaker. This quaternary ammonium composition has an approximate distribution of alkyl chain lengths ($C_{16}$, 2%; $C_{14}$, 95%; and $C_{12}$, 3%) and has antimicrobial properties. The beaker containing the powder was heated on a hot plate to about 160° F. with occasional stirring with a propeller-type agitator. The powder melted into a liquid. The resulting liquid quaternary ammonium composition was poured into an eight ounce bottle. Upon cooling, the composition formed a substantially solid, nonflowable and homogeneous antimicrobial composition.

EXAMPLE 2

A 200 g sample of BTC2125MP40™ (sold by Stepan Chemical Company) was placed in a 600 ml beaker and heated to about 250° F., at which point the powder melted to form a liquid. The quaternary ammonium salts contained in BTC2125MP40™ are known to have antimicrobial properties. The melted composition was then poured into an eight ounce bottle where it formed a substantially solid, nonflowable and homogeneous antimicrobial composition upon cooling. BTC2125MP40™ contains 20 percent n-alkyl dimethyl benzyl ammonium chloride ($C_{12}$, 5%; $C_{14}$, 60%; $C_{16}$, 30%; $C_{18}$, 5%), 20 percent n-alkyl dimethyl ethyl benzyl ammonium chloride ($C_{12}$, 68%; $C_{14}$, 32%) and 60 percent inert ingredients.

EXAMPLE 2A

About a 20 gram quantity of JAQ Powdered Quat™ is mixed with 60 grams Igepal DM-970™ (dinonylphenol ethoxylate where ethoxylate is over 100 moles of ethylene oxide, available from Rhone Poulenc) and heated to melt the mixture, thereby attaining a liquid. About 20 grams citric acid is then added, with mixing to disperse the citric acid in the mixture. The mixture is then poured into a container where upon cooling it solidifies into an acidic, substantially solid and homogeneous antimicrobial composition.

EXAMPLE 2B

About 85 grams Rhodasurf TB-970™ linear $C_{20-22}$ alcohol ethoxylate (Rhone Poulenc) is heated to a temperature of about 140° F. until melted. About 5 grams FMB451-8 Quat™ is then added and mixed until dispersed. Small amounts of dye and fragrance may also be added. The resulting dispersion is then poured into a container where it solidifies into an acidic, substantially solid and homogeneous antimicrobial composition upon cooling.

In general, acidic disinfectant compositions may include:

| | |
|---|---|
| Water soluble organic solid base | 0%–90% |
| Antimicrobial ingredient | 5%–50% |
| Acidic component | 5%–50% |

Water soluble organic bases include polyethylene glycols, alkyl phenol ethoxylates, and linear alcohol ethoxylates. Polyethylene glycols preferably have molecular weights greater than about 2000. Alkyl phenol ethoxylates ideally have about 4–100 ethylene oxide groups per molecule. Linear alcohol ethoxylates preferably have about 2–150 ethylene oxide groups per alcohol molecule.

Acidic components may include organic or inorganic acids. Suitable organic acids include citric acid, adipic acid, oxalic acid, sulfamic acid, gluconic acid and succinic acid. Inorganic acids may include hydrochloric acid, phosphoric acid and sulfuric acid, preferably as aqueous solutions.

EXAMPLE 3

A mixture of about 100 g of powder n-coco-1,3 diaminopropane (Duomeen C™, described above) and about 100 g of flaked coco monoethanolamine (Alkamide L203™ sold by Rhone Poulenc) was placed into a beaker and heated to a temperature of about 190° F., whereupon the mixture formed a liquid. The resulting liquid was poured into an eight fluid ounce bottle where it solidified upon cooling, thereby forming a substantially solid, nonflowable and homogeneous antimicrobial composition. Duomeen C™ is known to have antimicrobial activity.

EXAMPLE 3A

About 60 grams linear alcohol ethoxylate, preferably Neodol 25-12™ TM ($C_{12-15}$ alcohol, 12 mole ethoxylate), sold by Shell Chemical, is melted. Continuous mixing is commenced when the linear alcohol ethoxylate is sufficiently melted. About 300 grams BTC2125MP40™ is added and melts upon attaining a temperature of about 230° F. About 85 grams urea, 3 grams sodium carbonate, 508.5 grams sodium sulfate, and 10 grams precipitated silica are further added and mixed thoroughly to form a mixture. About 1.5 grams yellow dye and 5 grams fragrance are then added. The mixture is further agitated and heated until it reaches a temperature of about 220° F., at which point it becomes a liquid. The liquid is then poured into a container and allowed to cool and solidify, thus forming a substantially solid, nonflowable and homogeneous composition.

EXAMPLE 3B

About 85.5 grams linear alcohol ethoxylate, preferably Rhodasurf TB-970™ flake (described above), is heated to a temperature of about 140° F. until melted. Agitation or stirring is commenced upon melting. Also added are about 2.5 grams FMB451-8 Quat™ (described in Example 6) and 12.0 grams tetrasodium ethylenediaminetetraacetate. The resulting liquid mixture is then poured into a plastic container and allowed to cool, thereby forming a substantially solid, nonflowable and homogeneous antimicrobial composition.

EXAMPLE 4

Two hundred grams powdered orthobenzyl parachlorophenol, sold by Nipa Laboratories under the trademark Nipacide BCP™, with known antimicrobial properties, was heated slowly to a temperature of about 120° F. to form a liquid. The liquid was poured into an eight fluid ounce plastic bottle. Upon cooling, the compound formed a substantially solid, nonflowable and homogeneous antimicrobial composition in the bottle.

EXAMPLE 5

This example describes the production of a solid antimicrobial cleaning product. About 67.6 grams of JAQ™ brand n-alkyl dimethyl benzyl ammonium chloride dihydrate ($C_{16}$, 2%; $C_{14}$, 95%; and $C_{12}$, 3%), 27.8 g of nonylphenol (ethoxylate)$_{12}$, sold by Harcross under the trademark T-DET N-12™, and 30.0 g tetrasodium ethylenediaminetetraacetate (EDTA) were heated together to a temperature of about 160° F. The mixture was stirred with a propeller type mixer until fluid. While continuing agitation, the mixture was allowed to cool to about 140° F. Upon reaching 140° F., the mixture was poured into a plastic 76 fluid oz. bottle and allowed to further cool, whereupon a substantially solid, nonflowable and homogeneous composition formed.

EXAMPLE 6

Five hundred grams of FMB451-8 Quat™ was placed into a 1000 ml beaker and heated first to about 98° C. whereupon it began to boil. FMB451-8 Quat™ is a liquid antimicrobial product containing 80 percent by weight n-alkyl dimethyl benzyl ammonium chloride ($C_{12}$, 40%; $C_{14}$, 50%; and $C_{16}$, 10%) 12.5 percent ethanol and 7.5 percent water. The temperature was slowly raised to a maximum of about 150° C. and then maintained for about 30 minutes while the solvents evaporated.

After this period of evaporation, the beaker was removed from the heat and allowed to cool to about 100° C. The liquid became progressively more viscous as it cooled. The product was subsequently poured into a plastic 32 fluid oz. bottle. In the bottle, the composition further cooled to form a highly viscous, gel-like substance which did not flow. The final product was a substantially nonflowable and homogeneous antimicrobial composition with a weight of about 400 g indicating the loss of about 100 g of solvent from the evaporation process. Hence, essentially all of the solvent initially present in the liquid antimicrobial product was removed by the evaporation process.

EXAMPLE 7

About 350 g of anhydrous sodium tripolyphosphate was placed into a mixing vessel. A 280 g sample of liquid antimicrobial composition FMB1210-50™, sold by Crystal Performance Chemicals was added to the mixing vessel. The mixture was mixed in a paddle mixer until a free flowing, but viscous blend was formed. The mixture was then poured into a 76 fluid oz. plastic bottle. After standing for three days at room temperature, the composition formed a substantially solid, nonflowable and homogeneous antimicrobial composition.

EXAMPLE 8

The composition of Example 1 was prepared in a bottle. The bottle was placed in a dispenser similar to the dispenser shown in FIG. 1. An upward water spray dissolved a portion of the composition which was collected upon draining out of the funnel. The solution draining out of the funnel contained about 0.4750% or 4750 parts per million (ppm) of the quaternary ammonium salt. However, solutions with concentrations as high as 30,000 ppm have been achieved. The concentration was determined by titration using a commercially available test kit, for example, Taylor's™ test kit, K-1582 QAC(High) test™.

Since the solution was to be used as a sanitizer in a food handling operation, the desired concentration of the quaternary ammonium salt was nominally 200 ppm. To achieve the proper concentration, the solution was collected in a gallon jug as it drained from the funnel. A 5.5 fluid ounce quantity of the concentrate from the funnel was diluted to form 1 gallon of water, thereby achieving the desired 200 ppm concentration use solution. The final use solution was then sprayed onto pre-cleaned surfaces to kill any remaining micro-organisms.

EXAMPLE 9

The composition of Example 1 was again prepared in a bottle. The bottle was placed in a dispenser where the bowl was connected with a fresh water supply as described in U.S. Pat. No. 5,342,587 issued to Laughlin et al. The dispenser directed water at a surface of the substantially solid composition to dissolve a portion thereof. The concentrated solution draining from the bowl was mixed with fresh water to form a diluted use solution which flowed through a dispensing hose. The relative flow to the spray nozzle and the hose stream was adjusted to yield a 200 ppm solution as it exited the dispensing hose. The resulting use solution was sprayed from the dispensing hose onto surfaces to be sanitized, such as equipment, tables and fixtures in a food processing plant.

EXAMPLE 10

The cleaner-disinfecting composition of Example 5 was prepared in a bottle. The bottle was then inverted over a dispenser where the bowl connects with a fresh water supply, such as described in U.S. Pat. No. 5,342,587, issued to Laughlin, et al. A water spray dissolved a portion of the composition to form a solution which drained from the bowl. The concentrated solution combined with a connecting flow of clean water after leaving the bowl. The relative flow to the spray nozzle and the hose stream was adjusted to yield a 600 ppm use solution as it exited the dispensing hose. The concentration of quaternary ammonium salt was determined using a commercial test kit, as described above. The dispensing hose was used to deliver cleaner/disinfecting solution to a mop bucket for mopping floors or to another container such as a spray bottle. Mopping floors with this solution removed soils and left an antimicrobial residue. The antimicrobial residue killed any further microbes left on the floor, and further reduced odors and thereby prohibited the transmission of disease.

Various other modifications and alterations of this invention will become apparent to those skilled in the art. Thus, because numerous modifications may be made of this invention without departing from the spirit thereof, the scope of this invention is not to be limited to the embodiments and examples described herein. Rather, the scope of the invention is to be determined by appended claims and their equivalents.

I claim:

1. A process of making a substantially nonflowable disinfecting composition, the process comprising the steps of:

melting an alcohol alkoxylate selected from the group consisting of ethoxylates, propoxylates, and mixtures thereof to form a melt of the alcohol alkoxylate;

thereafter introducing to the melt of the alcohol alkoxylate, an antimicrobial composition, the antimicrobial composition including an antimicrobial compound, thereby forming a liquid, the antimicrobial compound selected from the group consisting of quaternary ammonium compounds, and cationic surfactants other than quaternary ammonium compounds, and mixtures thereof;

introducing a quantity of urea to the liquid mixture of the alcohol alkoxylate and the antimicrobial composition to form a liquid mixture of said alcohol alkoxylate, said antimicrobial composition and said urea;

pouring the liquid mixture of said alcohol alkoxylate, said antimicrobial composition and said urea into a container; and cooling the liquid mixture of said alcohol alkoxylate, said antimicrobial composition and said urea, thereby forming the substantially nonflowable disinfecting composition within the container, wherein said urea is introduced prior to the liquid mixture of alcohol alkoxylate and the antimicrobial composition being cooled.

2. The process of making a substantially nonflowable disinfecting composition according to claim 1, wherein the alcohol alkoxylate is a $C_{12-15}$ alcohol ethoxylate.

3. The process of claim 1, further comprising the steps of:

agitating the liquid mixture of said alcohol alkoxylate, said antimicrobial composition and said urea; and adding at least one cleaning agent selected from the group consisting of nonionic surfactants, anionic surfactants, alkaline builders, polyvalent metal sequestering agents and mixtures thereof.

* * * * *